United States Patent

(12) United States Patent
Eshima et al.

(10) Patent No.: US 11,524,078 B2
(45) Date of Patent: Dec. 13, 2022

(54) WATER-SOLUBLE MACROMOLECULAR DERIVATIVE OF VENETOCLAX

(71) Applicant: Delta-Fly Pharma, Inc., Tokushima (JP)

(72) Inventors: Kiyoshi Eshima, Tokushima (JP); Tatsuhiro Ishida, Tokushima (JP)

(73) Assignee: Delta-Fly Pharma, Inc., Tokushima (JP)

( * ) Notice: Subject to any disclaimer, the term of this patent is extended or adjusted under 35 U.S.C. 154(b) by 0 days.

(21) Appl. No.: 17/275,562

(22) PCT Filed: Jul. 17, 2020

(86) PCT No.: PCT/JP2020/027805
§ 371 (c)(1),
(2) Date: Mar. 11, 2021

(87) PCT Pub. No.: WO2021/229832
PCT Pub. Date: Nov. 18, 2021

(65) Prior Publication Data
US 2021/0386862 A1 Dec. 16, 2021

(51) Int. Cl.
*A61K 47/60* (2017.01)
*A61K 31/635* (2006.01)

(52) U.S. Cl.
CPC ............ *A61K 47/60* (2017.08); *A61K 31/635* (2013.01)

(58) Field of Classification Search
CPC ............................ A61K 47/60; A61K 31/635
See application file for complete search history.

(56) References Cited

U.S. PATENT DOCUMENTS

| 3,320,268 A | * | 5/1967 | Shen | .................... | C07D 471/04 |
| | | | | | 546/113 |
| 10,111,955 B2 | | 10/2018 | Eshima et al. | | |
| 2005/0112088 A1 | | 5/2005 | Zhao et al. | | |
| 2017/0368177 A1 | * | 12/2017 | Eshima | ................ | C08G 65/333 |
| 2019/0185471 A1 | | 6/2019 | Peddi Reddy et al. | | |

FOREIGN PATENT DOCUMENTS

| CN | 1852740 A | 10/2006 |
| CN | 104981245 A | 10/2015 |
| CN | 107001617 A | 8/2017 |
| CN | 107648185 A | 2/2018 |

(Continued)

OTHER PUBLICATIONS

Al Samad et al., "PCL-PEG graft copolymers with tunable amphiphilicity as efficient drug delivery systems," Journal of Materials Chemistry B, Aug. 30, 2016, 4(37):6228-6239.

(Continued)

*Primary Examiner* — Jianfeng Song
(74) *Attorney, Agent, or Firm* — Foley & Lardner LLP

(57) ABSTRACT

The present invention aims at providing novel means for administering Venetoclax, wherein the means reduces the burden on a patient caused by taking Venetoclax and achieves a good balance between the effect and safety of Venetoclax. The present invention relates to a water-soluble macromolecular derivative that includes a plurality of Venetoclaxs, each Venetoclax being linked to a terminal carboxyl group of a multi-arm water-soluble polymer via an amide bond.

4 Claims, 10 Drawing Sheets

(1) H-NMR SPECTRA OF COMPOUND OF FORMULA (I)

(2) H-NMR SPECTRA OF COMPOUND OF FORMULA (II)

(56) References Cited

FOREIGN PATENT DOCUMENTS

| | | |
|---|---|---|
| CN | 109563096 A | 4/2019 |
| EP | 3 333 167 A1 | 6/2018 |
| JP | 6542799 B2 | 6/2019 |
| RU | 2697551 C2 | 1/2019 |
| WO | WO-2016/088858 A1 | 6/2016 |
| WO | WO-2020/225738 A1 | 11/2020 |

OTHER PUBLICATIONS

Decision to Grant dated Nov. 10, 2020 in JP 2020-084919, with English translation.
International Search Report dated Aug. 25, 2020 in PCT/JP2020/027805.
Perez et al., "Etirinotecan pegol (NKTR-102) versus treatment of physician's choice in women with advanced breast cancer previously treated with an anthracycline, a taxane, and capecitabine (BEACON): a randomized, open-label multicenter, phase 3 trial," Lancet Oncol., 2015, 16(15):1556-1568.
Sparreboom et al., "Comparative Preclinical and Clinical Pharmacokinetics of a Cremophor-Free, Nanoparticle Albumin-Bound Paclitaxel (ABI-007) and Paclitaxel Formulated in Cremophor (Taxol)," Clinical Cancer Research, Jun. 1, 2005, 11(11):4136-4143.
Li et al., "A Review of Developments of the Selective BCL-2 Inhibitor Venetoclax," Journal of Inner Mongolia Medical University, Jun. 30, 2017, 39(3):283-287.
Office Action dated Oct. 8, 2021 in CN 202080005631.6, with English translation.
Supplementary European Search Report dated Jun. 10, 2022 in EP 20861942.9.

* cited by examiner (1) H-NMR SPECTRA OF COMPOUND OF FORMULA (I)

(2) H-NMR SPECTRA OF COMPOUND OF FORMULA (II)

RFU: relative fluorescence unit (1)

(2)

CHANGE OF BAX EXPRESSION (1) 
10 mg/ml (2) 
20 mg/ml    10 mg/ml

WATER-SOLUBLE MACROMOLECULAR DERIVATIVE OF VENETOCLAX

CROSS-REFERENCE TO RELATED APPLICATIONS

This application is the U.S. National Stage of PCT/JP2020/027805, filed Jul. 17, 2020, which claims priority to JP 2020-084919, filed May 14, 2020.

TECHNICAL FIELD

The present invention relates to a medicament or a method for treating or ameliorating cancer, wherein the medicament contains, as an active ingredient, a water-soluble macromolecular derivative of Venetoclax in which Venetoclax is linked to an end of a multi-arm water-soluble polymer.

BACKGROUND ART

Venetoclax has the effect of selectively binding to and inhibiting Bcl-2. Overexpression of Bcl-2 is observed in many cancers and this inhibits the process of natural death and/or self-destruction (apoptosis) of cancer cells. Venetoclax has the effect of inhibiting Bcl-2, thereby restoring the process of apoptosis in cancer cells. Venetoclax has been clinically applied as a therapeutic agent for relapsed and refractory chronic lymphocytic leukemia and for de novo acute myelocytic leukemia for which strong chemotherapy is not indicated. However, Venetoclax has a high binding percentage to human protein (99.9% or more) and also a low oral absorption percentage, resulting in an excessive single oral dose. Thus, in some cases, cancer patients had difficulty in taking Venetoclax. Furthermore, some patients experienced a strong side effect such as neutropenia after taking Venetoclax, and therefore, there were some cases when strict medication teaching by a doctor was essential for guaranteeing the safety of cancer patients adequately.

Most of the patients suffering from relapsed and refractory chronic lymphocytic leukemia or from de novo acute myelocytic leukemia for which strong chemotherapy is not indicated are both physically weak and old. Thus, a drastic improvement that facilitates administration of Venetoclax and reduces a side effect thereof has been awaited.

Currently, as described below, there are some known methods for increasing the usefulness of a poorly water-soluble anticancer agent as a pharmaceutical agent by using a water-soluble macromolecular substance to enhance water solubility of the anticancer agent.

(1) Abraxane (Non Patent Literature 1) is made by including paclitaxel in albumin derived from human blood to increase an intravenous dose of paclitaxel, thereby increasing the effect of reducing tumor size. Abraxane is approved as a therapeutic agent for advanced and recurrent breast cancer, stomach cancer, non-small cell lung cancer, and pancreatic cancer. However, since albumin derived from human blood is used, a risk for developing a disease such as hepatitis and AIDS infection cannot be eliminated completely. Supply of albumin derived from human blood is limited, and thus a problem of a stable supply thereof remains unsolved. It is still unclear whether synthetic albumin which can be manufactured by genetic engineering can be used in place of natural albumin or not.

(2) NKTR-102 (Non Patent Literature 2) is composed of a derivative of a polyethylene glycol compound and irinotecan linked via glycine. The polyethylene glycol compound has four polyethylene glycol chains and has a molecular weight of 40000 (also referred to as "multi-arm PEG"), and the derivative thereof is a compound in which four terminal hydroxyl groups of the four chains are replaced by —OCH$_2$COOH (also referred to as "multi-arm CTPEG"). The multi-arm CTPEG is bound via glycine to a hydroxyl group of irinotecan with an ester bond. NKTR-102 has previously been clinically developed for, for example, patients with advanced and recurrent breast cancer. However, NKTR-102 is susceptible to metabolic degradation by a degradative enzyme such as esterase and carboxylase in human blood, and thus, a dose of NKTR-102 needed to be increased greatly to ensure an adequate effect thereof. Consequently, toxicity was increased and the therapeutic effect of irinotecan which was an existing drug could not be improved. Thus, NKTR-102 was not approved as a new drug.

(3) Patent Literatures 1 to 3 by the present inventors disclose a water-soluble macromolecular derivative of an anticancer substance, wherein the anticancer substance having an amino group is linked via an amide bond to multi-arm CTPEG serving as a water-soluble macromolecule.

CITATION LIST

Patent Literature

[Patent Literature 1]
Japanese Patent No. 6542799
[Patent Literature 2]
U.S. patent Ser. No. 10/111,955
[Patent Literature 3]
Russian Patent No. 2697551

Non Patent Literature

[Non Patent Literature 1]
Sparreboom A et al., Clinical Cancer Research, 2005; (11): 4136-4143
[Non Patent Literature 2]
Edith A Perez et al., The Lancet Oncology, 2015; (16): 556-1568

SUMMARY OF INVENTION

Technical Problem

It is an object of the present invention to provide novel means for administering Venetoclax, wherein the means reduces the burden on a patient (for example, an excessive dose and a side effect) caused by taking Venetoclax and achieves a good balance between effect and safety of Venetoclax.

Solution to Problem

The present inventors conducted intensive research to solve the above described problem. Consequently, the present inventors have found that a compound obtained by linking each of plural Venetoclaxs via an amide bond to an end of a multi-arm water-soluble polymer has a higher water solubility compared to conventional Venetoclax, can act on cancer cells efficiently, and can reduce the burden on a patient caused by taking Venetoclax.

Specifically, the present invention encompasses the following invention.

[1] A compound including a plurality of Venetoclaxs, each Venetoclax being linked to an end of a multi-arm water-soluble polymer via an amide bond; or a pharmacologically acceptable salt thereof.

[2] The compound according to [1], wherein the compound results from amide-forming condensation between a terminal carboxyl group of the multi-arm water-soluble polymer and a secondary amino group on a pyrrole ring of the plurality of Venetoclaxs; or a pharmacologically acceptable salt thereof.

[3] The compound according to [1] or [2], wherein the multi-arm water-soluble polymer is a multi-arm carboxyl-terminated polyethylene glycol; or a pharmacologically acceptable salt thereof.

[4] The compound according to [3] represented by the following formula (II):

[5] A pharmaceutical composition for treating or ameliorating cancer, wherein the pharmaceutical composition includes the compound according to any of [1] to [4]; or a pharmacologically acceptable salt thereof.

[6] The pharmaceutical composition according to [5], wherein the cancer is a hematologic cancer.

[7] The pharmaceutical composition according to [6], wherein the hematologic cancer is acute myelocytic leukemia or chronic lymphocytic leukemia.

[8] The compound according to any of [1] to [4] for using in a method for treating or ameliorating cancer; or a pharmacologically acceptable salt thereof.

[9] The compound according to [8], wherein the cancer is a hematologic cancer; or a pharmacologically acceptable salt thereof.

[10] The compound according to [9], wherein the hematologic cancer is acute myelocytic leukemia or chronic lymphocytic leukemia; or a pharmacologically acceptable salt thereof.

[Formula 1]

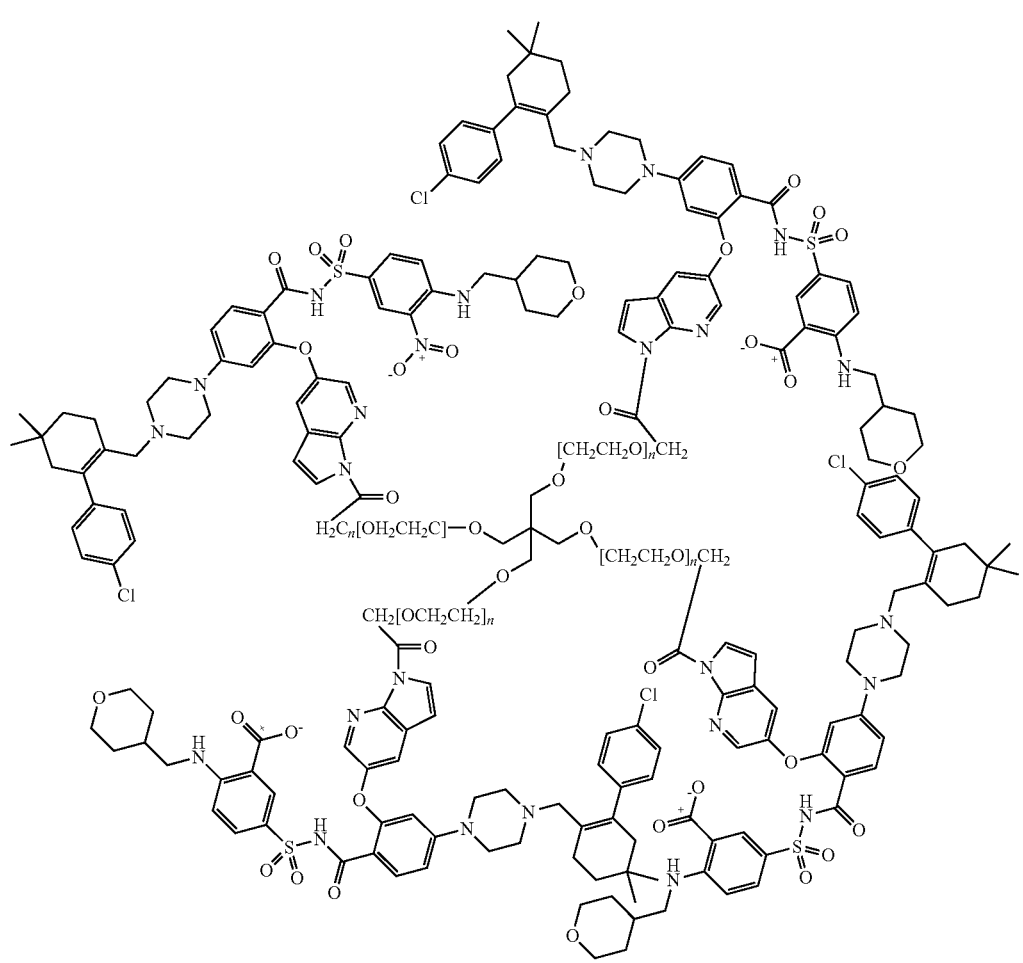

Formula (II)

wherein n represents a number of 50 to 2000; or a pharmacologically acceptable salt thereof.

[11] A method for treating or ameliorating cancer, the method including administering to a patient the compound according to any of [1] to [4] or a pharmacologically acceptable salt thereof.

[12] The method according to [11], wherein the cancer is a hematologic cancer.

[13] The method according to [12], wherein the hematologic cancer is acute myelocytic leukemia or chronic lymphocytic leukemia.

[14] Use of the compound according to any of [1] to [4] or a pharmacologically acceptable salt thereof in manufacturing a medicament for treating or ameliorating cancer.

[15] The use according to [14], wherein the cancer is a hematologic cancer.

[16] The use according to [15], wherein the hematologic cancer is acute myelocytic leukemia or chronic lymphocytic leukemia.

This specification encompasses the content described in the specification and/or drawings of Japanese Patent Application No. 2020-084919, to which the present application claims priority.

All publications, patents, and patent applications cited herein are incorporated herein by reference in their entirety.

Advantageous Effects of Invention

The present invention can provide novel means for administering Venetoclax, wherein the means reduces the burden on a patient (for example, an excessive dose and a side effect) caused by taking Venetoclax and achieves a good balance between effect and safety of Venetoclax.

The present invention can also provide Venetoclax as a pharmaceutical agent that can be administered intravenously and has enhanced safety.

BRIEF DESCRIPTION OF DRAWINGS

FIG. 1(2) is an H-NMR chart, which confirms the chemical structural formula of a compound of formula (II).

FIG. 10(1) shows the results obtained with the culture media containing the compound of formula (I) or the compound of formula (II) at specified concentrations; and FIG. 10(2) shows the results of measurement of caspase activity when the compound of formula (I) or the compound of formula (II) were used at a concentration of 0.1 µM.

FIG. 11(2) shows a photograph of a uniform aqueous solution of the compound of formula (II) prepared by adding the compound to physiological saline at 40° C. to 50° C. and performing a procedure such as sonication treatment to obtain a final concentration of 10 mg/ml or 20 mg/ml.

DESCRIPTION OF EMBODIMENTS

Figure 1:
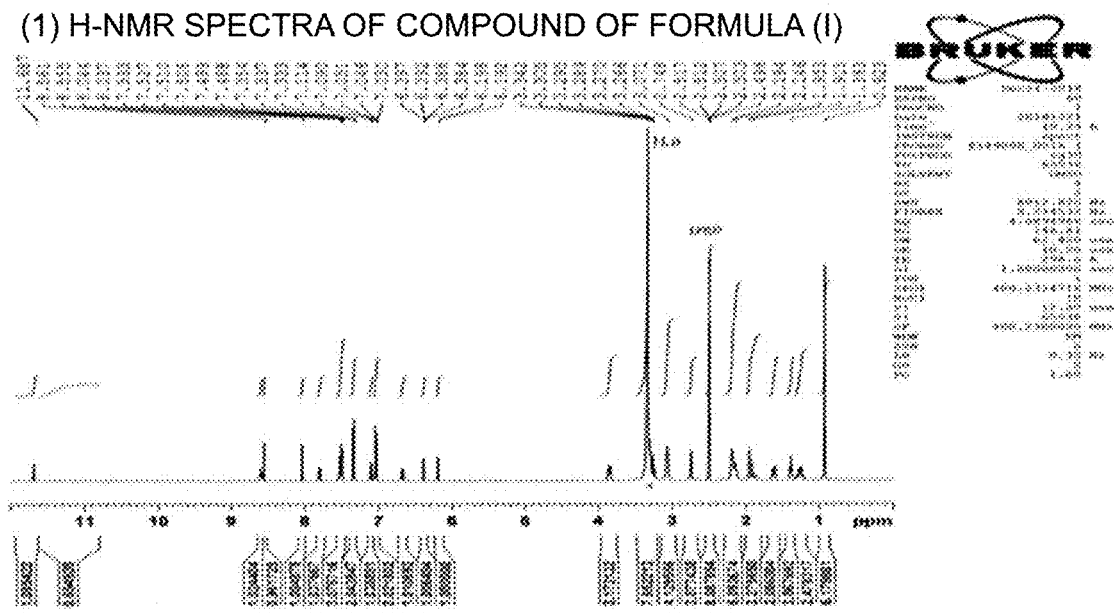
FIG. 1(1) is a proton nuclear magnetic resonance (hereinafter referred to as "H-NMR") chart, which confirms the chemical structural formula of a compound of formula (I).
Figure 1:
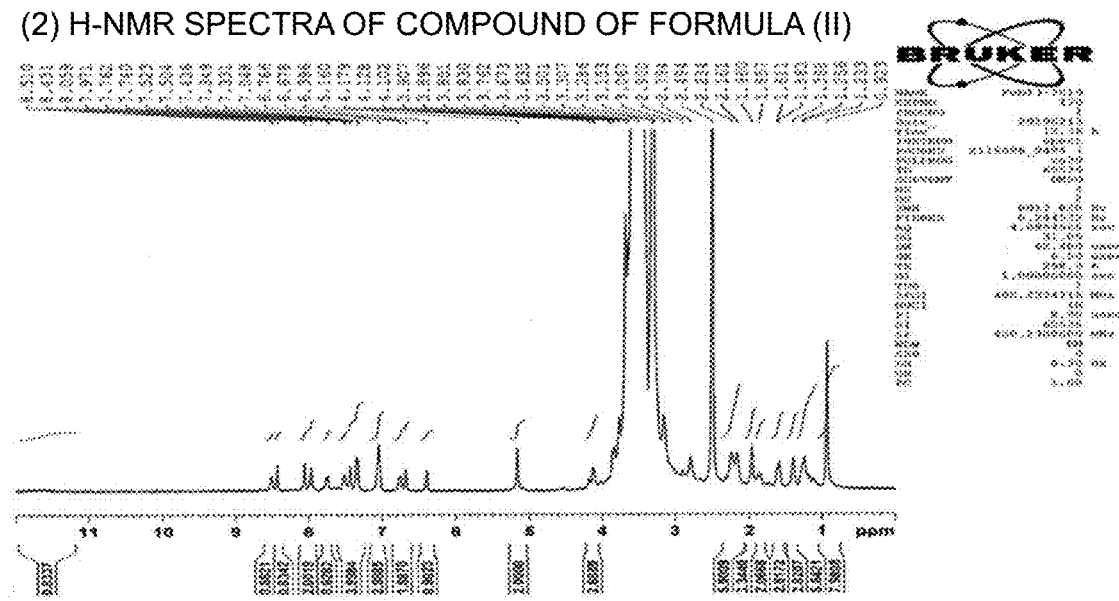

The present invention relates to a compound including a plurality of Venetoclaxs, each Venetoclax being linked via an amide bond to an end of a multi-arm water-soluble polymer (hereinafter also referred to as "compound of the present invention"); or a pharmacologically acceptable salt thereof; wherein the compound can be used as an active ingredient in a medicament for treating or ameliorating cancer and a method for treating or ameliorating cancer.

"Venetoclax" is a compound represented by the following formula (I).

[Formula 2]

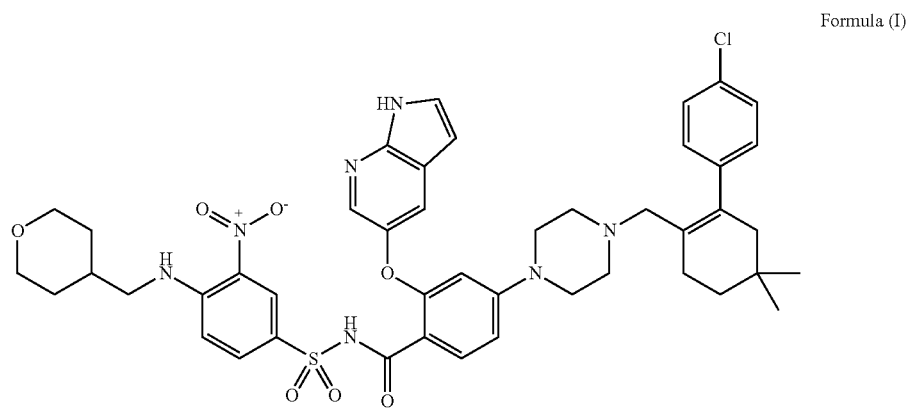

Formula (I)

Venetoclax is a compound used as an active ingredient of Venclexta® which is a therapeutic agent for relapsed or refractory chronic lymphocytic leukemia (including small lymphocytic lymphoma). In the present invention, Venetoclax synthesized industrially according to a conventional known technique may be used, or commercial Venetoclax for use in a pharmaceutical agent may be used. Herein, the compound of formula (I) may be described simply as "Venetoclax."

"Multi-arm water-soluble polymer" means a structure consisting of a plurality of (for example, 2, 3, 4, 5, 6, 7, 8, or more) water-soluble polymers (also referred to as "arms"), one end of the polymer being connected to a core which is an atom, a molecule, or an entity. The arm may be a linear polymer or a branched polymer. The branched polymer may be a highly branched polymer (also referred to as "dendritic polymer" or "hyperbranched polymer"). The water-soluble polymer serving as the arm may be any biodegradable polymer. Examples of such water-soluble polymer include polyethylene glycol (may be described as "PEG" herein), polyacrylic acid, polymaleic acid, polyethyleneimine, polycarboxyvinyl, polyvinyl alcohol, polyvinylpyrrolidone, polypropylene glycol, and carboxymethyl cellulose, and hydroxymethylcellulose (but not limited thereto). The weight-average molecular weight of the multi-arm water-soluble polymer is about 3 kDa to about 100 kDa; and can be, for example, about 4 kDa to about 80 kDa, about 5 kDa to about 60 kDa, about 8 kDa to about 40 kDa, or about 10 kDa to about 20 kDa. All the plurality of arms may be identical water-soluble polymers. Alternatively, water-soluble polymers of different types or different lengths may be used in combination.

In the present invention, the multi-arm water-soluble polymer may be the one having a carboxyl group at one end (the end not connected to the core) of each arm. Carboxylation of the end of the water-soluble polymer can be performed by using a conventional technique.

It is preferable that the multi-arm water-soluble polymer used in the present invention be a multi-arm CTPEG that has, as arms, 2 to 8, preferably 2, 4, 6, or 8, and more preferably 4 carboxyl-terminated PEGs (may be described as "CTPEG" herein). The multi-arm CTPEG can be obtained by linking CTPEG of various weight-average molecular weights to, for example, a pentaerythritol core via a spacer if needed. Commercially available multi-arm CTPEG can be used. For example, such CTPEG is available from JenKem Technology.

The multi-arm water-soluble polymer and Venetoclax can be linked via an amide bond that is formed as a result of a condensation reaction between the terminal carboxyl group of each arm of the multi-arm water-soluble polymer and an amino group of Venetoclax. Linking the multi-arm water-soluble polymer and Venetoclax via an amide bond is believed to allow Venetoclax to act in vivo. Specifically, in the body, an enzyme such as protease (for example, caspase) that catalyzes hydrolysis of the amide bond acts on the polymer-linked Venetoclax to separate Venetoclax which is an active ingredient from the multi-arm water-soluble polymer, and thus, Venetoclax can act. The amino group of Venetoclax used for linkage to the multi-arm water-soluble polymer may be any amino group, but a secondary amino group on a pyrrole ring is preferably used.

In one embodiment, the compound of the present invention is a compound represented by the following formula (II).

[Formula 3]

Formula (II)

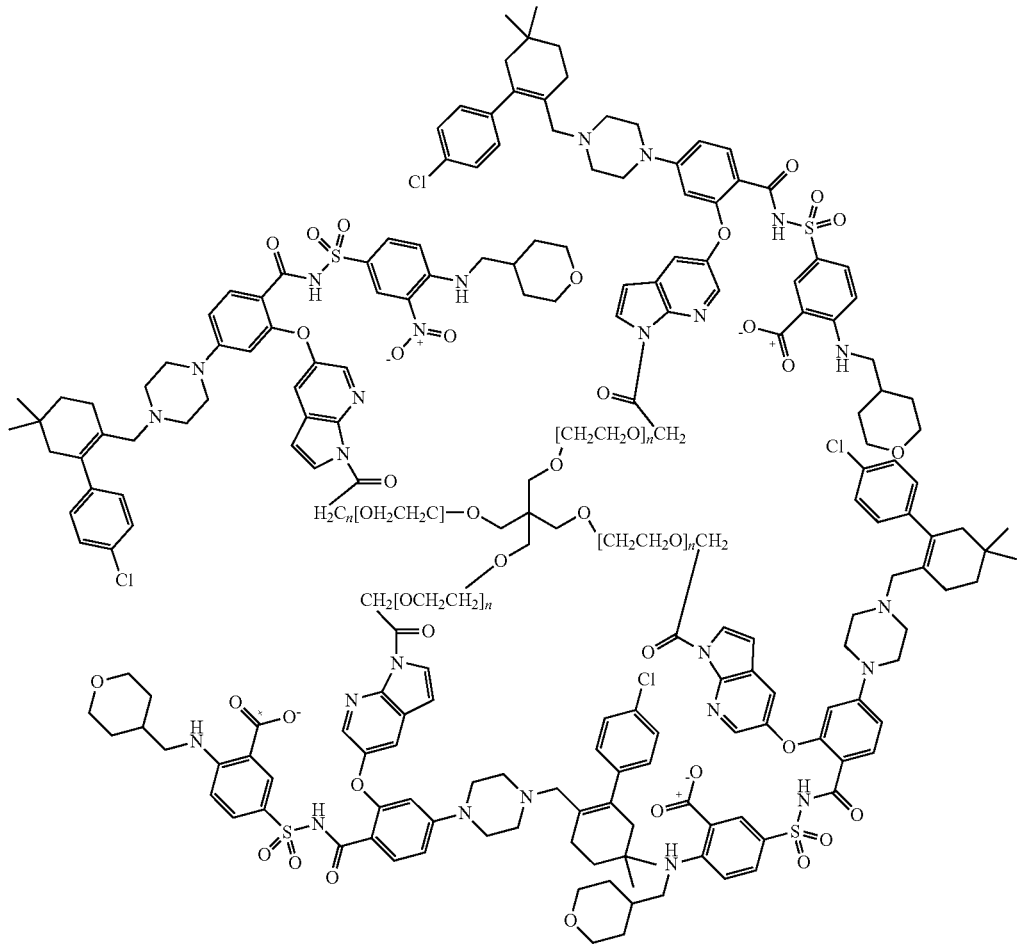

Specifically, this compound has a structure in which Venetoclax is linked at the secondary amino group on the pyrrole ring thereof to each end of the multi-arm PEG having four arms via an amide bond. In the above formula, n may be, but not particularly limited to, 50 or more. For example, n is 50 to 2000, preferably 100 to 2000, more preferably 150 to 1000, still more preferably 200 to 500, and particularly preferably 230. Additionally or alternatively, the weight-average molecular weight of this compound is, but not particularly limited to, for example, 10 kDa to 60 kDa, preferably 20 kDa to 60 kDa, and particularly preferably 40 kDa. Herein, the compound of formula II may be described as "PEG-Venetoclax."

A "pharmacologically acceptable salt" refers to a salt whose administration to a living body is acceptable and examples thereof include an acid addition salt and a base addition salt. Examples of "acid addition salt" include a hydrochloride salt, a sulfate salt, a nitrate salt, a phosphate salt, a hydrobromide salt, a carbonate salt, an acetate salt, a trifluoroacetate salt, p-toluenesulfonate salt, a propionate salt, a tartrate salt, a fumarate salt, a malate salt, a maleate salt, a citrate salt, and a methanesulfonate salt (but not limited thereto). Examples of "base addition salt" include an alkali metal salt (for example, a sodium salt and a potassium salt), an alkaline earth metal salt (for example, a calcium salt), a magnesium salt, and an ammonium salt (but not limited thereto).

The above described compound of the present invention or a pharmacologically acceptable salt thereof can be used as an active ingredient in the method for treating or ameliorating cancer and in a pharmaceutical composition for treating or ameliorating cancer.

In the present invention, examples of "cancer" include, but not limited to, a hematologic cancer and a solid cancer (brain tumor and glioma, pituitary adenoma, acoustic neurinoma, uveal malignant melanoma, meningioma, pharyngeal cancer, laryngeal cancer, tongue cancer, thyroid cancer, breast cancer, lung cancer, thymoma, thymic carcinoma, mesothelioma, esophageal cancer, stomach cancer, colon cancer, hepatoma, bile duct cancer, pancreatic cancer, renal cell carcinoma, bladder cancer, prostate cancer, renal pelvis and ureter cancer, penile cancer, testicular tumor (orchioncus), uterine cancer, ovarian cancer, vulvar cancer, skin cancer, malignant melanoma (skin), basal cell carcinoma, a precursor to skin cancer, intraepidermal cancer, squamous cell carcinoma, mycosis fungoides, malignant bone tumor (osteosarcoma), soft tissue sarcoma, chondrosarcoma, malignant fibrous histiocytoma, and the like) and metastatic cancers thereof. Preferably, "cancer" in the context of the present invention is a hematologic cancer and a metastatic cancer thereof. A "hematologic cancer" refers to cancer that begins in a hematopoietic organ and examples thereof include, but not limited to, acute myelocytic leukemia (AML), chronic myelocytic leukemia (CML), acute lymphocytic leukemia (ALL), chronic lymphocytic leukemia (CLL), myeloproliferative neoplasm (MPN), malignant lymphoma, and multiple myeloma. In the present invention, more preferably, the hematologic cancer is acute myelocytic leukemia (AML) or chronic lymphocytic leukemia.

"Treating or ameliorating cancer" used in the context of the present invention not only refers to a status where cancer has completely disappeared but also refers to a status where cancer has shrunk or disappeared temporarily or permanently and/or a stable status where cancer does not worsen. For example, this phrase encompasses one or more of reduction in size of the cancer, reduction in the tumor marker level, improvement of symptoms associated with cancer, increase in a parameter such as overall survival, progression-free survival, and median survival.

The compound of the present invention or a pharmacologically acceptable salt thereof may be used by itself (alone) or in the form of a pharmaceutical composition (hereinafter, may be described as "pharmaceutical composition of the present invention") in the method for treating or ameliorating cancer. The pharmaceutical composition is combined with an excipient, a binder, a disintegrant, a lubricant, and the like, which are generally used in the manufacture of medicament and is formulated into a dosage form suitable for an intended administration route.

Examples of the excipient include a saccharide (a monosaccharide, a disaccharide, cyclodextrin, and a polysaccharide such as alginic acid), a metallic salt, kaolin, silicic acid, polyethylene glycol, and a mixture thereof.

Examples of the binder include simple syrup, glucose solution, starch solution, gelatin solution, polyvinyl alcohol, polyvinyl ether, polyvinylpyrrolidone, carboxymethyl cellulose, shellac, methylcellulose, ethylcellulose, and a mixture thereof.

Examples of the disintegrant include dried starch, sodium alginate, powdered agar, powdered laminaran, sodium hydrogencarbonate, calcium carbonate, polyoxyethylene sorbitan fatty acid esters, sodium lauryl sulfate, monoglyceride stearate, starch, lactose, and a mixture thereof.

Examples of the lubricant include purified talc, a stearate salt, borax, polyethylene glycol, and a mixture thereof.

If necessary, the pharmaceutical composition may additionally include a diluent, a stabilizer, an isotonizing agent, a pH adjuster, a buffer, a solubilizing agent, a suspending agent, a colorant, a flavoring agent, an odor-masking agent, a coating agent, a preservative, an antiseptic, an antioxidant, and the like, which are generally used in the manufacture of a medicament, as appropriate.

As one example, the pharmaceutical composition of the present invention can be formulated into a dosage form suitable for oral administration and can be provided as, for example, a tablet, a pill, a capsule, a granule, a powder, a syrup, and a suspension. The formulation in a solid dosage form can be coated as needed (for example, a sugar-coated tablet, a gelatin-coated tablet, and an enteric coated tablet).

As another example, the pharmaceutical composition of the present invention can be formulated into a dosage form suitable for parenteral administration and can be provided as, for example, an injection and an infusion formulation. These dosage forms may be those that are provided in a lyophilized storable state and are used after being prepared to an appropriate concentration by reconstitution with, for example, water or buffer such as saline before use.

The dose and administration route of the compound of the present invention or a pharmacologically acceptable salt thereof, or the pharmaceutical composition of the present invention may vary depending on factors such as the type and/or seriousness of cancer, the age, body weight, and condition of the patient. An amount sufficient to treat or ameliorate cancer can be administered by any administration route (oral administration or parenteral administration).

For example, the compound of the present invention or a pharmacologically acceptable salt thereof, or the pharmaceutical composition of the present invention can be administered parenterally at a dose selected from 50 to 1000 mg/kg, preferably 100 mg/kg to 500 mg/kg in terms of the above described compound of the present invention, which is an active ingredient, at a frequency of once every one to three weeks, and more preferably once every week. Examples of "parenteral administration" may include intravenous administration (such as intravenous injection and intravenous infusion), subcutaneous injection, intradermal injection, and intramuscular injection. Preferably, the compound of the present invention or a pharmacologically acceptable salt thereof, or the pharmaceutical composition of the present invention can be used for intravenous administration. For example, the above described amount can be administered intravenously over a period of 5 minutes to 120 minutes, preferably 10 minutes to 60 minutes, more preferably 15 minutes to 30 minutes, and particularly preferably 20 minutes.

The compound of the present invention or a pharmacologically acceptable salt thereof, or the pharmaceutical composition of the present invention can be used not only by itself (alone) but also in combination with an anticancer agent and/or radiotherapy used for treating or ameliorating cancer. Examples of the anticancer agent include an anticancer chemotherapeutic agent, an anticancer molecular target drug, and an anticancer immunotherapeutic agent. "Combination" in the context of the present invention includes not only simultaneous administration of respective ingredients but also sequential administration by which respective ingredients are administered at respective predetermined intervals over a treatment period. The administration route and means of administration of the respective ingredients to be administered in combination may be identical or different. Examples of the anticancer agent to be administered in combination may include cytarabine, azacytidine, decitabine, Vyxeos, cyclophosphamide, thiotepa, ifosfamide, busulfan, dacarbazine, melphalan, ranimustine, nimustine, doxorubicin, aclarubicin, idarubicin, daunorubicin, mytomycin C, pirarubicin, epirubicin, peplomycin, amrubicin, mercaptopurine, fludarabine, hydroxycarbamide, methotrexate, cladribine, enocitabine, rituximab, dasatinib, bortezomib, tamibarotene, ibritumomab, tretinoin, gemtuzumab ozogamicin, enasidenib, glasdegib, quizartinib, nivolumab (product name: Opdivo®), pembrolizumab (product name: Keytruda®), Ipilimumab (product name: Yervoy®), and atezolizumab (product name: Tecentriq®) (but not limited thereto). One or more anticancer agents can be selected as appropriate depending on factors such as the type and/or seriousness of cancer and the age, body weight, and condition of the patient.

When used in combination, the anticancer agent can be administered by a dosage regimen that includes a shorter administration period and/or an extended rest period and a reduced dose which is 90%, 80%, 70%, 60%, 50% 40%, or less based on the dose when used by itself. This can allow for suppressing or delaying the occurrence of side effects that may be caused by administration of the anticancer agent (for example, without limitation, myelosuppression, hemolytic anemia, disseminated intravascular coagulation syndrome, fulminant hepatic failure, dehydration, enteritis, interstitial pneumonia, stomatitis, gastrointestinal ulceration, gastrointestinal bleeding, gastrointestinal perforation, acute renal failure, muco-cutaneo-ocular syndrome, toxic epidermal necrolysis, neuropsychiatric disorder, acute pancreatitis, rhabdomyolysis, and anosmia); and/or significantly reducing a cancer patient's financial burden and a financial burden of medical insurance on the country or a local government associated with use of anticancer agents.

The present invention further relates to a method for treating or ameliorating cancer that includes administering the compound of the present invention or a pharmacologically acceptable salt thereof, or the pharmaceutical composition of the present invention to a cancer patient. Cancers to be treated or ameliorated by this method and the dosage regimen of the compound of the present invention or a pharmacologically acceptable salt thereof, or the pharmaceutical composition of the present invention are described above.

EXAMPLES

Hereinafter, the present invention will be described specifically with reference to Examples, but the present invention is not limited to these Examples.

[Example 1] Synthesis and Analysis of Compound of Formula (II)

Figure 2:
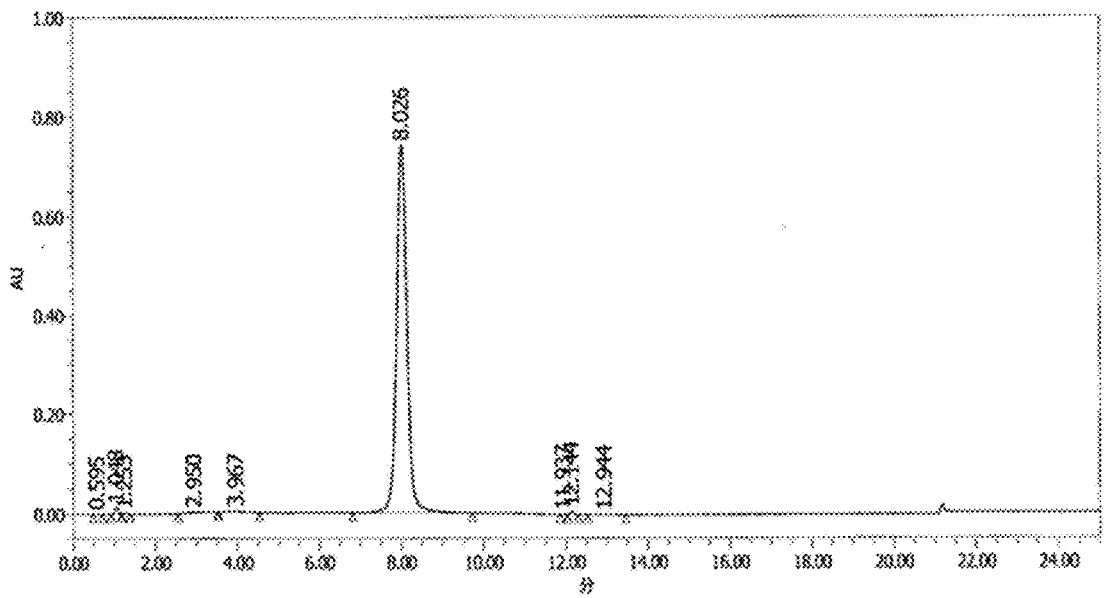
FIG. 2 is a chromatogram of high performance liquid chromatography (hereinafter referred to as "HPLC"), which shows purity and impurities of the compound of formula (II). The purity and the amount of the impurities are shown below the figure.

Under nitrogen atmosphere, CTPEG (4.530 g, one equivalent) was added to 55 mL of DMF solvent and heated at 50° C. to obtain a homogenous solution. N,N-diisopropylethylamine (hereinafter referred to as "DIC") (0.296 g, 20 equivalents), 1-hydroxybenzotriazole (hereinafter referred to as "HOBT") (0.258 g, 6 equivalents), and Venetoclax (0.474 g, 4.8 equivalents) were added sequentially to the solution. This mixture was continuously stirred for 6 hours at 60° C. and then cooled to 40° C. Then, while stirring, methyl tetra-butyl ether (hereinafter referred to as "MTBE") preheated to 30° C. was added dropwise over 20 minutes. After cooling over 60 minutes and then stirring for 30 minutes, generated crystals were collected by filtration and washed with 20 mL of MTBE. The obtained crystals were dissolved in 20 mL of absolute ethanol preheated to 40° C. and 70 mL of MTBE was added to the solution dropwise over 20 minutes. After cooling to 0° C. over 60 minutes and then stirring for 30 minutes, generated precipitates were collected by filtration. This purification procedure by recrystallization was repeated several times by using the same process. The material obtained was dried for 5 hours or more in a vacuum desiccator at 35° C. and was subjected to HPLC analysis. HPLC analysis showed that the purity of the compound of formula (II) was 97% or more, with the amount of each impurity being 1% or less. Thus, the material was placed in a plastic bag filled with nitrogen gas and stored at −20° C. The chemical structure of the compound of formula (II) thus obtained and the chemical structure of the compound of formula (I) were identified by H-NMR analysis (see FIG. 1). Furthermore, a high purity of the compound of formula (II) was confirmed by HPLC analysis (see FIG. 2).

[Example 2] Cytotoxic Effect of Compound of formula (I) and Compound of formula (II)

Concentration dependence of the cytotoxic effect of the compound of formula (I) and the compound of formula (II) was examined as described below.

Figure 3:
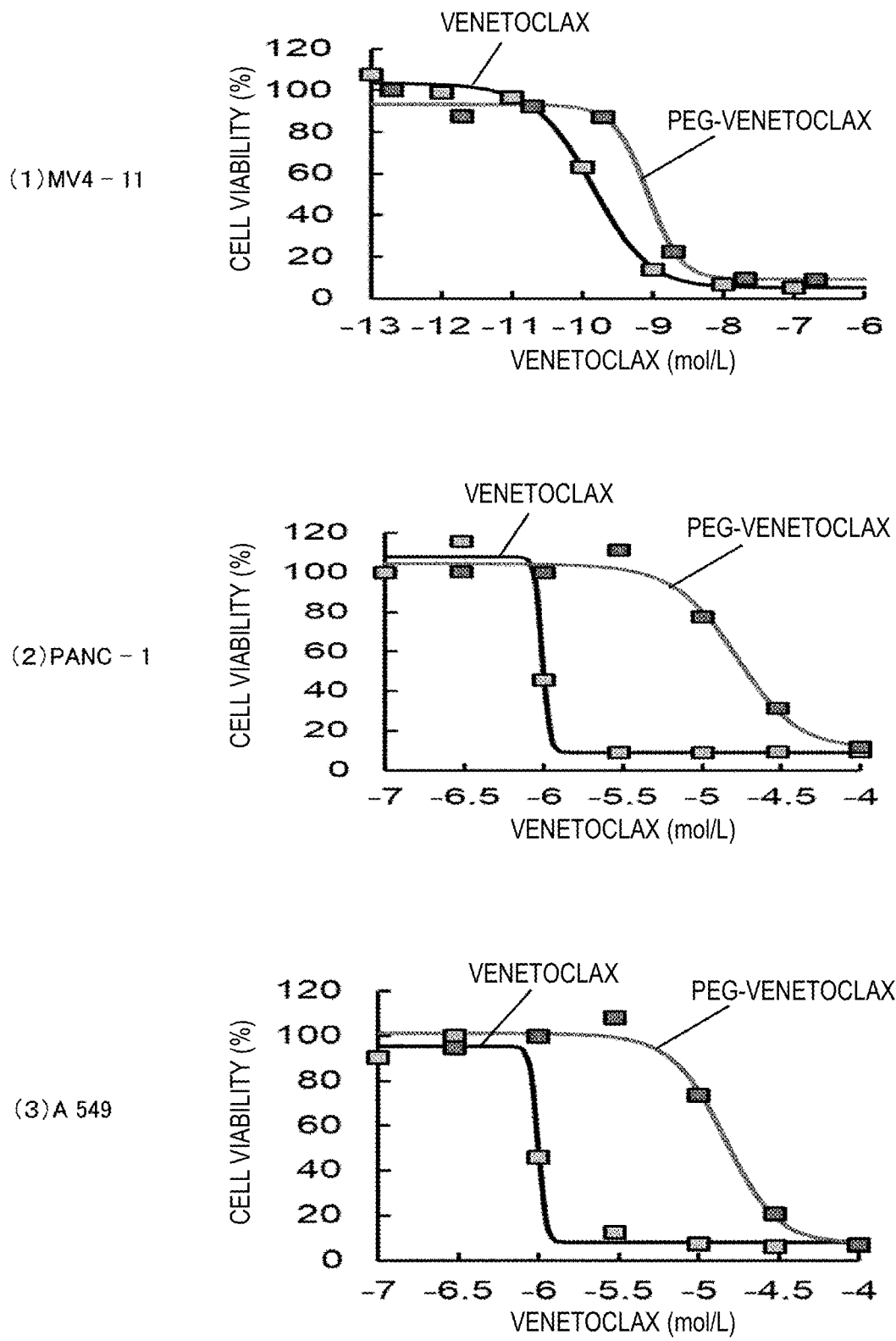
FIG. 3 is a graph showing concentration dependence of the cytotoxic effect of the compound of formula (I) and the compound of formula (II). The figures show the results obtained by using (1) a human acute myelocytic leukemia cell line MV4-11, (2) a human pancreatic cancer cell line PANC-1, and (3) a human lung cancer cell line A549, respectively.

$IC_{50}$ (50% inhibition percentage) of the compound of formula (I) and the compound of formula (II) was measured by using a human acute myelocytic leukemia cell line MV4-11(see FIG. 3(1)). The results showed that both compounds had a high inhibition percentage, with $IC_{50}$ (50% inhibition percentage) of the compound of formula (I) being 0.16 pM and $IC_{50}$ of the compound of formula (II) being 0.85 pM. Note that a culture medium containing reduced blood serum (Opti-MEM) was used for measurement of the compound of formula (I) due to a high percentage binding to protein (99.9% or more) thereof.

$IC_{50}$ (50% inhibition percentage) of the compound of formula (I) and the compound of formula (II) was measured by using a human pancreatic cancer cell line PANC-1 (see FIG. 3(2)). It was found that $IC_{50}$ of the compound of formula (I) was 0.99 μM and $IC_{50}$ of the compound of formula (II) was 18.9 μM.

$IC_{50}$ (50% inhibition percentage) of the compound of formula (I) and the compound of formula (II) was measured by using a human lung cancer cell line A549 (see FIG. 3(3)). It was found that $IC_{50}$ of the compound of formula (I) was 0.99 μM and $IC_{50}$ of the compound of formula (II) was 15.5 μM.

Figure 4:
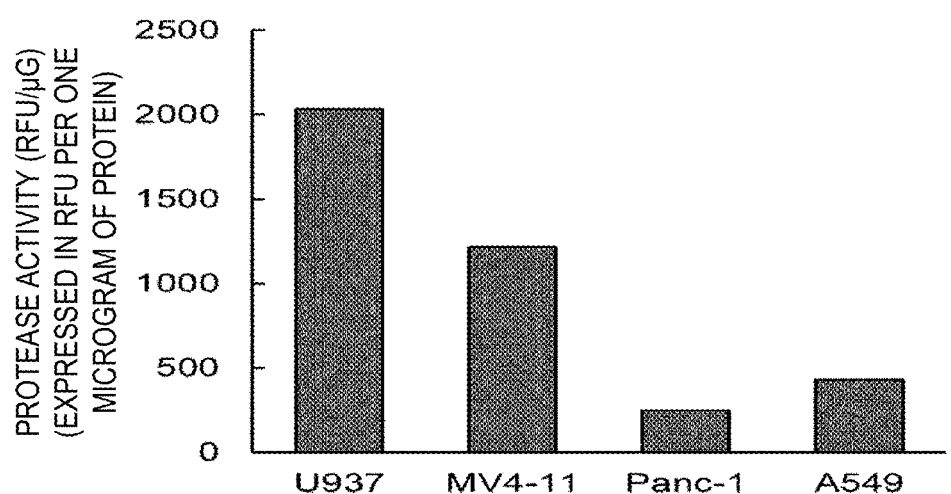
FIG. 4 is a graph showing protease activity of U937 (human histiocytic lymphoma cell line), MV4-11 (human acute myelocytic leukemia cell line), PANC-1 (human pancreatic cancer cell line), and A549 (human lung cancer cell line).

[Example 3] Cytotoxic Effect of Compound of formula (II) and Protease Activity of Cancer Cells Protease activity of U937 (human histiocytic lymphoma cell line), MV4-11 (human acute myelocytic leukemia cell line), PANC-1 (human pancreatic cancer cell line), and A549 (human lung cancer cell line) was measured and the results are shown in FIG. 4. Protease activity was measured by using "Amplite™ Universal Fluorimetric Protease Activity Assay Kit *Green Fluorescence*" available from AAT Bioquest, Inc., and fluorescence intensity obtained was expressed as a value based on the protein amount measured by "DC protein assay" available from Bio-Rad Laboratories, Inc. This study showed that a correlation was observed between the 50% inhibitory concentrations of the compound of formula (II) for MV4-11, PANC-1, and A549 measured in above described Example 2 and the protease activity of these cancer cell lines. Specifically, it was confirmed that the higher the protease activity of cancer cells was, the higher an inhibition percentage of the compound of formula (II) was. This suggested that the amide bond of the compound of formula (II) was enzymatically broken down around the cancer cells with a higher protease activity, resulting in selective release of the compound of formula (I).

[Example 4] Effect in Mouse Model of Human Acute Myelocytic Leukemia (OCI-AML-2)

Figure 5:
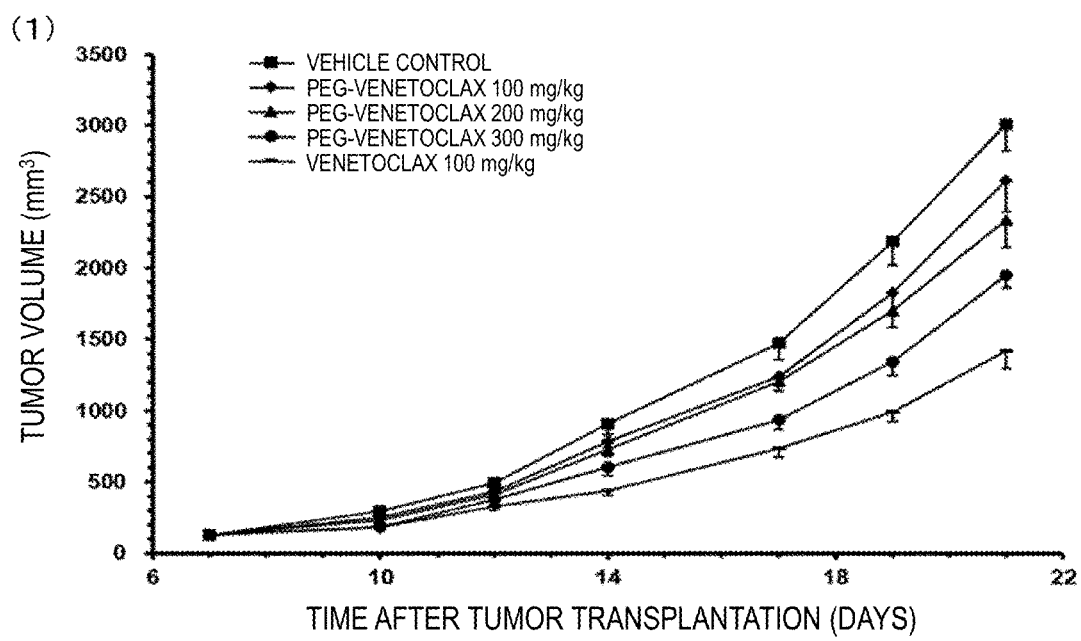
FIG. 5 is a graph showing (1) the effect of the compounds on suppressing tumor growth and (2) the effect of the compounds on suppressing weight change in mice groups as measured by using mice models which were generated by transplanting the human acute myelocytic leukemia cell line OCI-AML-2 subcutaneously into mice. The mice groups were the following: a control group; groups whose mice received the compound of formula (II) intravenously once every week for two weeks at a dose of 100 mg/kg, 200 mg/kg, or 300 mg/kg; and a group whose mice received the compound of formula (I) orally every day for two weeks at a dose of 100 mg/kg.
Figure 5:
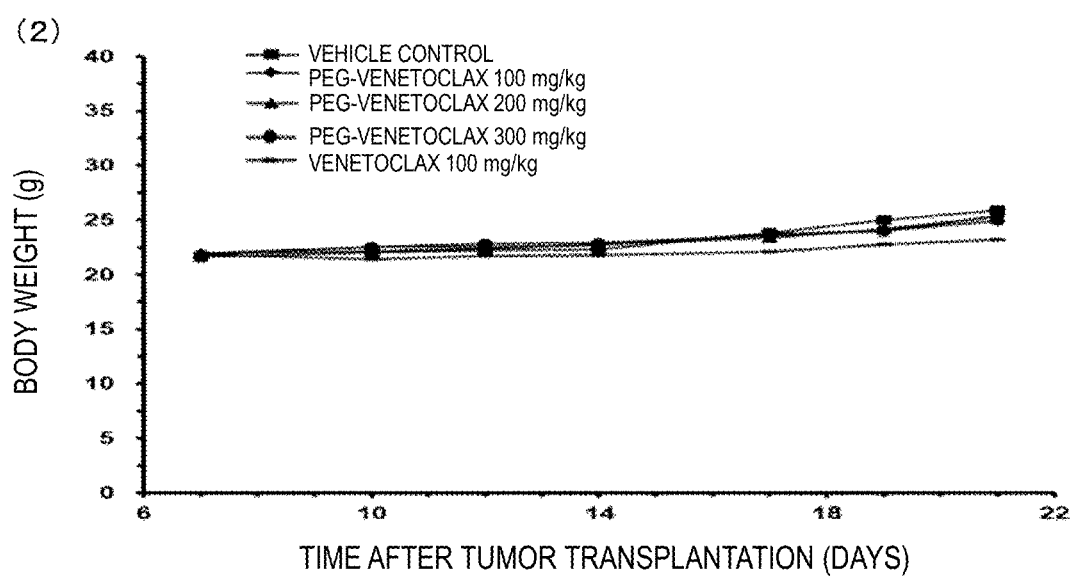

The effects of the compounds on suppressing tumor growth were compared in mice groups by using mice models which were generated by transplanting a human acute myelocytic leukemia cell line OCI-AML-2 subcutaneously into mice. The mice groups were the following: a control group; groups whose mice received the compound of formula (II) intravenously once every week for two weeks at a dose of 100 mg/kg, 200 mg/kg, or 300 mg/kg; and a group whose mice received the compound of formula (I) orally every day for two weeks at a dose of 100 mg/kg (see FIG. 5(1)).

The results indicated that the compound of formula (II) inhibited growth of tumor in a dose-dependent manner at all the doses of 100 mg/kg, 200 mg/kg, and 300 mg/kg. Furthermore, the compound of formula (II) hardly suppressed weight change at all the doses and the weight change was almost the same as that of the control group. The compound of formula (I) suppressed weight change (see FIG. 5(2)).

The total dose of the compound of formula (I) was 1,400 mg/kg (daily administration for two weeks at a dose of 100 mg/day), while the total dose of the substance of formula (II) was 16 mg/kg, 32 mg/kg, and 48 mg/kg (doses in terms of the compound of formula (I)). The effect of the compound of formula (II) on inhibiting tumor growth was comparable to that of the compound of formula (I) when the compound of formula (II) was administered at one thirty-fifths the dose of the compound of formula (I). Safety was also studied based on suppression of weight change and was found to be high.

[Example 5] Effect in Mouse Model of Human Acute Myelocytic Leukemia (MV4-11)

The effects of the compounds on suppressing tumor growth were compared in three groups by using animal models which were generated by transplanting a human acute myelocytic leukemia cell line MV4-11 subcutaneously into mice. The mice groups were the following: a control group; a group whose mice received the compound of formula (II) intravenously at a frequency of once a week for three weeks at a dose of 300 mg/kg (at a dose of 24 mg/kg in terms of the substance of formula (I)); and a group whose mice received the compound of formula (I) orally every day for three weeks at a dose of 50 mg/kg.

Figure 6:
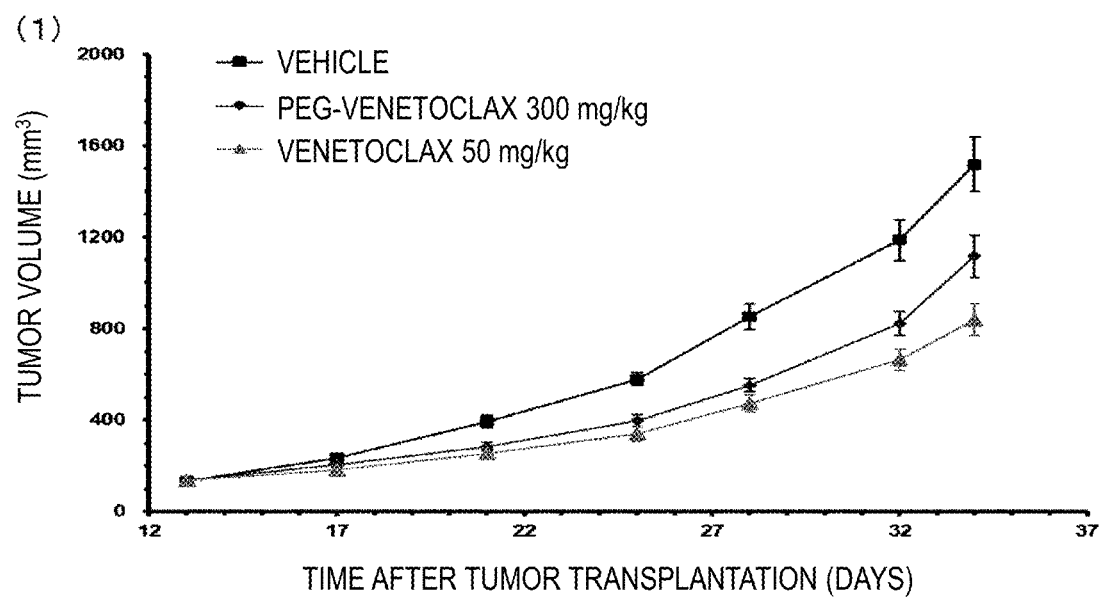
FIG. 6 is a graph showing (1) the effect of the compounds on suppressing tumor growth and (2) the effect of the compounds on suppressing weight change in mice groups as measured by using mice models which were generated by transplanting the human acute myelocytic leukemia cell line MV4-11 subcutaneously into mice. The mice groups were the following: a control group; a group whose mice received the compound of formula (II) intravenously once every week for three weeks at a dose of 300 mg/kg; and a group whose mice received the compound of formula (I) orally every day for three weeks at a dose of 50 mg/kg.
Figure 6:
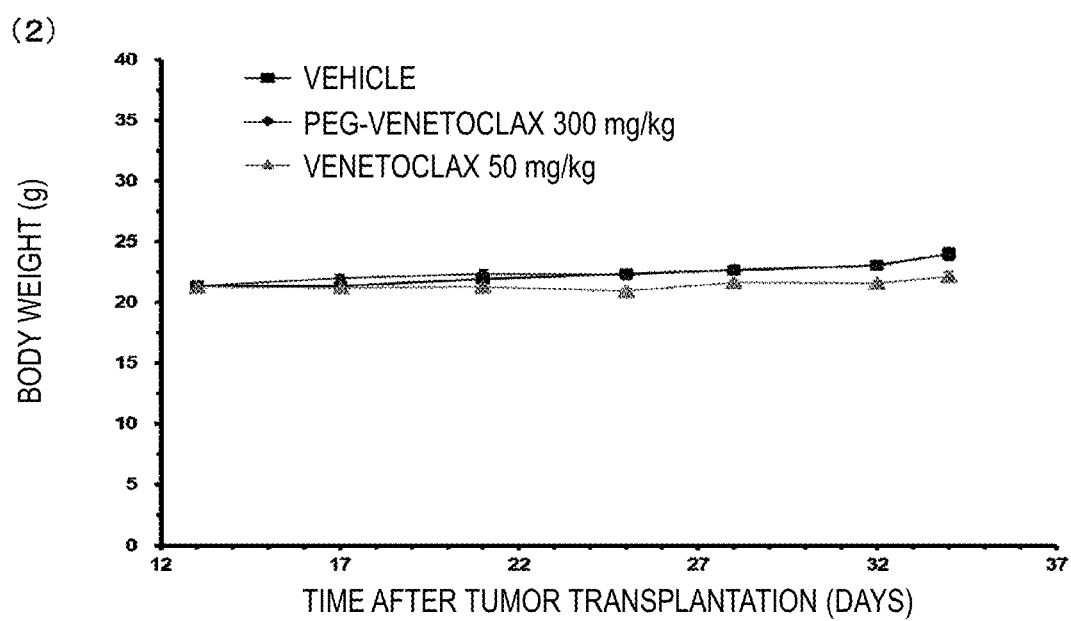

The results indicated that the effect of inhibiting tumor growth of the compound of formula (II) was comparable to that of the compound of formula (I) although the total dose of the compound of formula (II) over three weeks (72 mg/kg) was much less (one fifteenth) compared to the total dose of the compound of formula (I) over three weeks (1,050 mg/kg) (see FIG. 6(1)). It was also found that the compound of formula (II) was safer than the compound of formula (I) (see FIG. 6(2)).

[Example 6] Effect in Mouse Model of Human Histiocytic Lymphoma

The effects of the compounds on suppressing tumor growth were compared in three groups by using mice models which were generated by transplanting a human histiocytic lymphoma cell line U937 subcutaneously into mice. The three groups were the following: a control group; a group whose mice received the compound of formula (II) intravenously at a frequency of once a week for two weeks at a dose of 200 mg/kg or 300 mg/kg; and a group whose mice received the compound of formula (I) orally every day for two weeks at a dose of 100 mg/kg.

Figure 7:
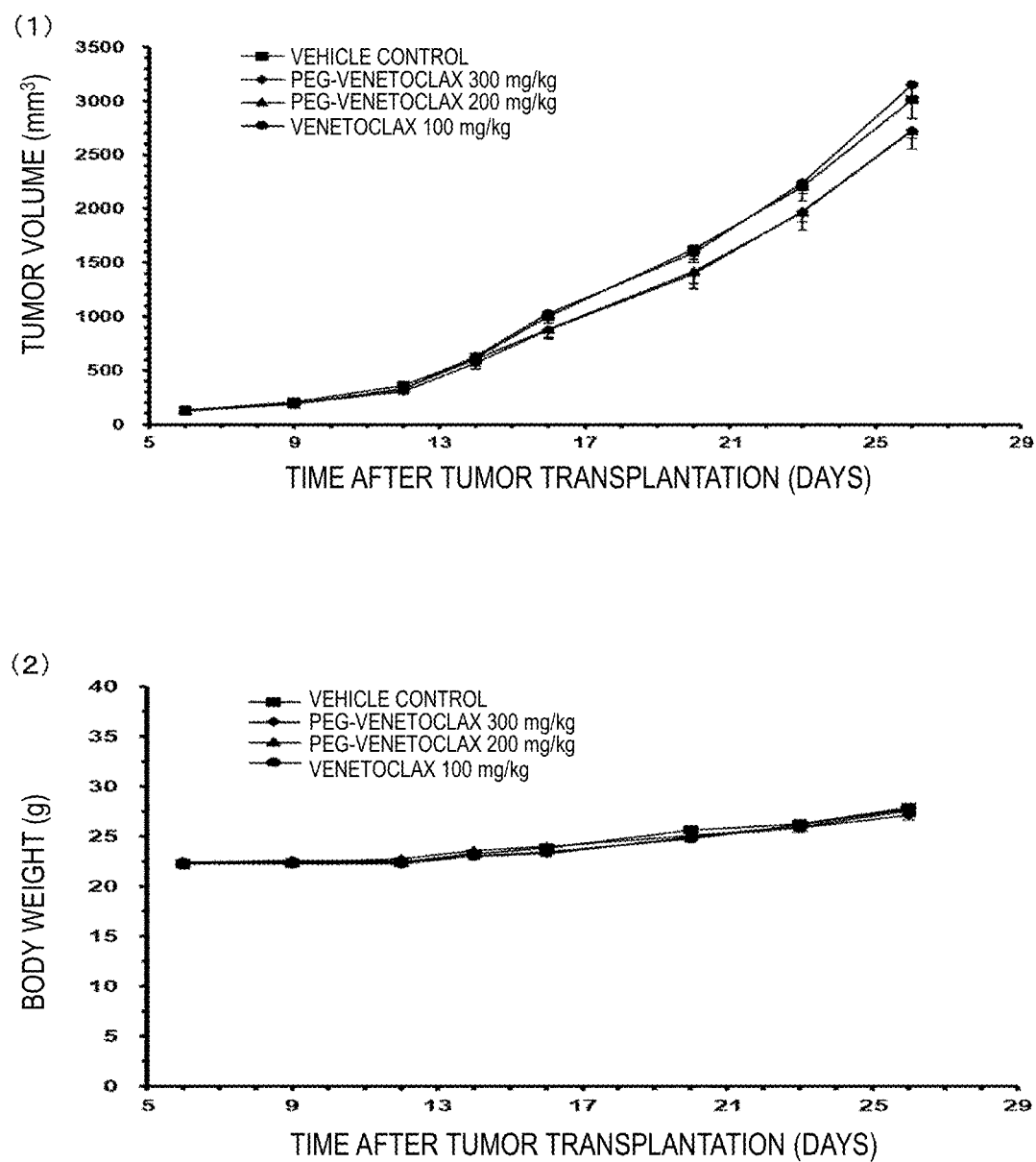
FIG. 7 is a graph showing (1) the effect of the compounds on suppressing tumor growth and (2) the effect of the compounds on suppressing weight change in mice groups as measured by using mice models which were generated by transplanting the human histiocytic lymphoma cell line U937 subcutaneously into mice. The mice groups were the following: a control group; groups whose mice received the compound of formula (II) intravenously once every week for two weeks at a dose of 200 mg/kg or 300 mg/kg; and a group whose mice received the compound of formula (I) orally every day for two weeks at a dose of 100 mg/kg.

No group showed a significant effect of suppressing tumor growth (see FIG. 7(1)). Furthermore, there was no difference in the effect of suppressing weight change among the groups (see FIG. 7(2)). U937 (human histiocytic lymphoma cell line) exhibited the strongest protease activity as described in Example 3 but the compound of formula (I) had no effect of suppressing growth of U937 (human histiocytic lymphoma cell line). This result suggested that although protease cleaved the amide bond of the compound of formula (II) to release the compound of formula (I) abundantly in the vicinity of tumor cells, it failed in exerting the effect of suppressing tumor growth.

[Example 7] Change of Expression of Apoptosis-Inducing Protein BAX/BAK

Pharmaceutical Interview Form (The Japanese Society of Hospital Pharmacists, issued in November 2019 (the second edition)) of Venclexta® tablet 10 mg, Venclexta® tablet 50 mg, and Venclexta® tablet 100 mg describes as follows: "Venetoclax is an orally administrable low molecular weight substance that selectively inhibits BCL-2 which is an apoptosis-inhibiting protein. BCL-2 functions in an apoptosis-inhibiting manner by interacting with pro-apoptotic protein (such as BAX/BAK and BIM). Venetoclax is believed to exhibit an anti-tumor effect by directly binding to BCL-2, thereby releasing pro-apoptotic protein which induces tumor cells to proceed to rapid apoptosis." Although BAX is a protein expressed in cytoplasm, BAX is reported to accumulate in the outer membrane of mitochondria when apoptosis is induced by inhibition of BCL-2.

Human acute myelocytic leukemia cells MV4-11 were plated on a culture medium and cultured overnight. Then, the compound of formula (I) was added at concentrations of 0.1 µM and 1 µM, and the compound of formula (II) was added at concentrations of 0.01 µM, 0.1 µM, and 1 µM. After incubation for five hours, a cytoplasm fraction and a mitochondrial fraction were extracted and BAX expression was examined.

Figure 8:
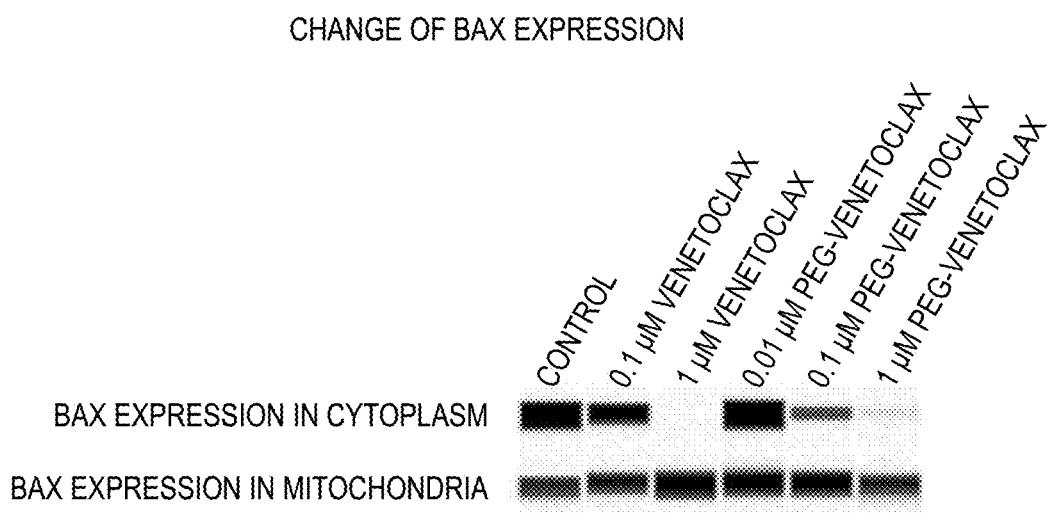
FIG. 8 shows the result of measurement of the BAX amount in a mitochondrial fraction and a cytosolic fraction obtained from the human acute myelocytic leukemia cells MV4-11 that were cultivated in a culture medium containing the compound of formula (I) or the compound of formula (II).

The results showed that, in both cases of the compound of formula (I) and the compound of formula (II), a concentration-dependent decrease of BAX in the cytoplasm fraction was observed (see FIG. 8).

[Example 8] Change in Amount of Released Cytochrome C

In the above described Pharmaceutical Interview Form, "cytochrome C" that flowed out from mitochondria into cytoplasm is described as "pro-apoptotic protein." Therefore, human acute myelocytic leukemia cells MV4-11 were plated on a culture medium and cultured overnight. Then, the compound of formula (I) was added at concentrations of 0.1 µM and 1 µM, and the compound of formula (II) was added at concentrations of 0.01 µM, 0.1 µM, and 1 µM. After incubation for five hours, a cytoplasm fraction and a mitochondrial fraction were extracted and cytochrome C release was examined.

Figure 9:
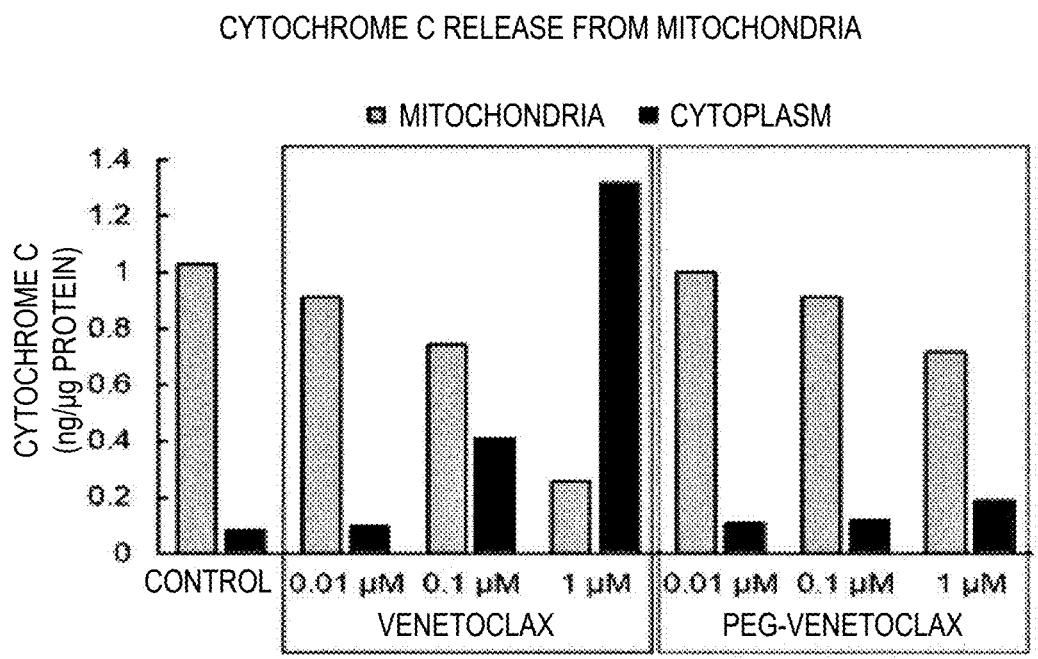
FIG. 9 shows the result of measurement of the cytochrome C amount in a mitochondrial fraction and a cytosolic fraction obtained from the human acute myelocytic leukemia cells MV4-11 that were cultivated in a culture medium containing the compound of formula (I) or the compound of formula (II).

The results showed that the amount of cytochrome C released from mitochondria into cytoplasm increased depending on the concentration of the compound of formula (I) added and depending on the concentration of the compound of formula (II) added (see FIG. 9).

[Example 9] Change of Caspase Activity

According to the above described Pharmaceutical Interview Form, cytochrome C that flowed out from mitochondria into cytoplasm activates caspase, thereby inducing apoptosis. Therefore, human acute myelocytic leukemia cells MV4-11 were plated on a culture medium and cultured overnight. Then, the compound of formula (I) was added at concentrations of 1 pM, 0.01 nM, 0.1 nM, 1 nM, 0.01 µM, 0.1 µM, and 1 µM; and the compound of formula (II) was added at concentrations of 1 pM, 0.01 nM, 0.1 nM, 1 nM, 0.01 µM, and 0.1 µM. After incubation for 24 hours, the culture medium was collected and caspase activity was examined by a conventional known technique.

Figure 10:
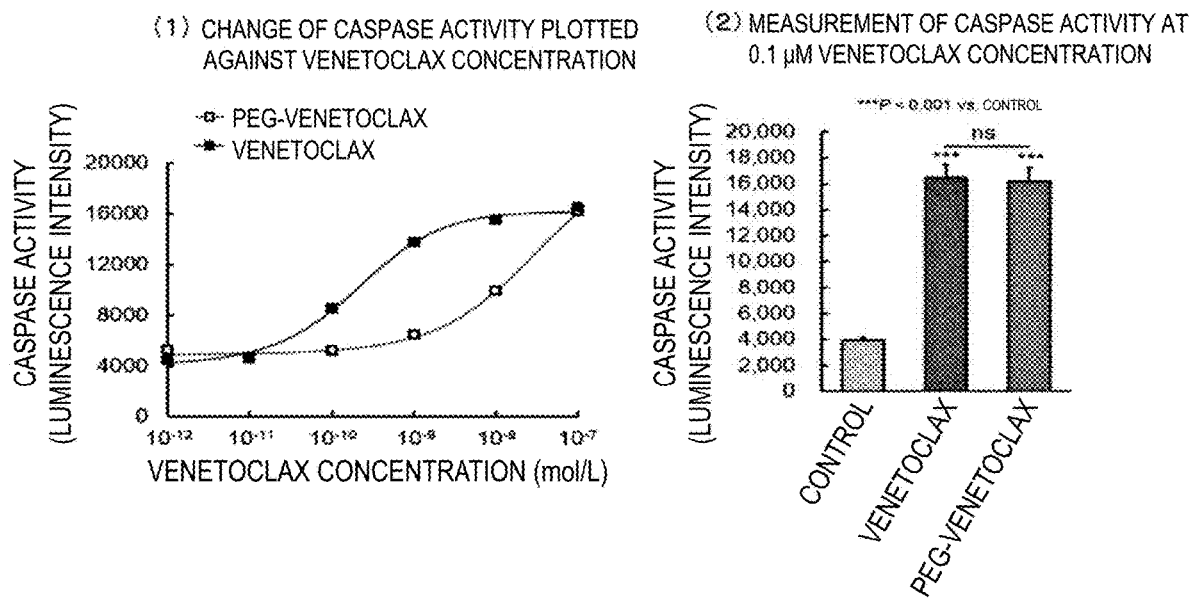
FIG. 10 shows the result of measurement of caspase activity of the human acute myelocytic leukemia cells MV4-11 that were cultivated in a culture medium containing the compound of formula (I) or the compound of formula (II).

The results showed that caspase activity increased depending on the concentration of the compound of formula (I) added and depending on the concentration of the compound of formula (II) added (see FIG. 10(1)). When the concentration in terms of Venetoclax was 0.1 μM, exactly the same caspase activity was observed in both cases of the compound of formula (I) and the compound of formula (II) (see FIG. 10(2)). This finding confirmed that the compound of formula (II) exhibited an anti-tumor effect by inhibiting BCL-2, thereby inducing apoptosis of tumor cells, in the same manner as the compound of formula (I).

[Examples 10] Solubility in Water of Compounds

Figure 11:
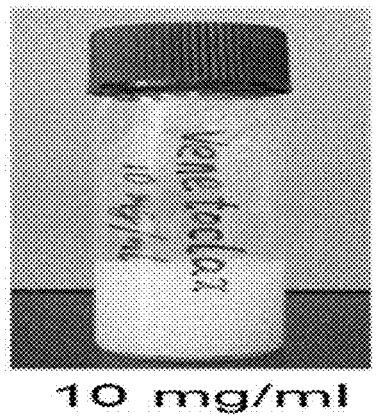
FIG. 11(1) shows a photograph of a solution of the compound of formula (I) prepared by adding the compound to physiological saline containing 5% CMC (carboxymethyl cellulose) and suspending the compound uniformly at a concentration of 10 mg/ml by a procedure such as sonication treatment.
Figure 11:
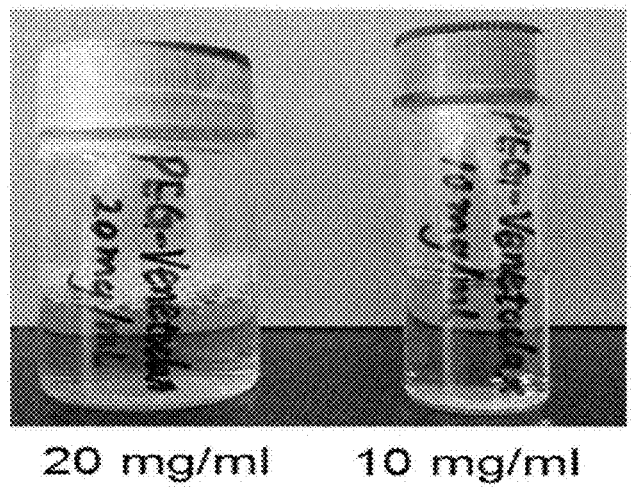

The compound of formula (I) was added to physiological saline containing 0.5% CMC (carboxymethyl cellulose) and a procedure such as sonication treatment was performed to obtain a uniform bright yellow opaque suspension at a concentration of 10 mg/mL (see FIG. 11(1)).

On the other hand, when the compound of formula (II) was added to physiological saline at 40° C. to 50° C. and the procedure such as sonication treatment was performed, uniform transparent yellow aqueous solutions at concentrations of 10 mg/mL and 20 mg/mL were obtained and no precipitation occurred even after the aqueous solutions were brought to room temperature. A high solubility in water of the compound of formula (II) was confirmed (see FIG. 11(2)).

The invention claimed is:

1. A compound comprising a plurality of Venetoclaxs, each Venetoclax being linked to an end of a multi-arm water-soluble polymer via an amide bond; or a pharmacologically acceptable salt thereof, wherein the compound is represented by the following formula (II):

Formula (II)

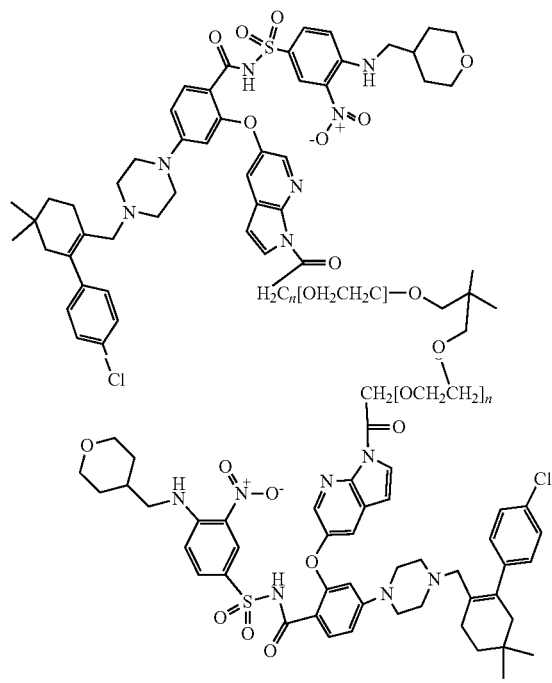

-continued

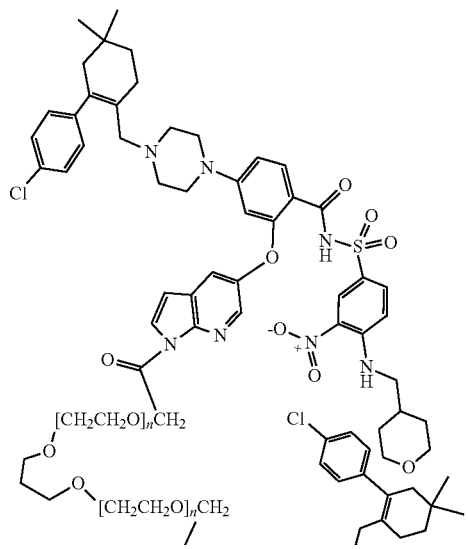

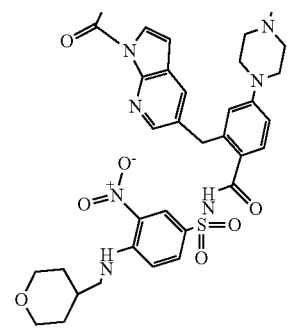

wherein n represents a number of 50 to 2000.

2. A pharmaceutical composition, wherein the pharmaceutical composition comprises the compound according to claim 1 or a pharmacologically acceptable salt thereof.

3. The compound according to claim 1, wherein a weight-average molecular weight of the multi-arm water-soluble polymer is about 3 kDa to about 100 kDa.

4. The compound according to claim 1, wherein a weight-average molecular weight of the multi-arm water-soluble polymer is about 10 kDa to about 20 kDa.

* * * * *

UNITED STATES PATENT AND TRADEMARK OFFICE
CERTIFICATE OF CORRECTION

| | | |
|---|---|---|
| PATENT NO. | : 11,524,078 B2 | |
| APPLICATION NO. | : 17/275562 | |
| DATED | : December 13, 2022 | |
| INVENTOR(S) | : Kiyoshi Eshima and Tatsuhiro Ishida | |

It is certified that error appears in the above-identified patent and that said Letters Patent is hereby corrected as shown below:

On the Title Page

Add the following:
--(30) Foreign Application Priority Data
May 14, 2020 (JP) ........................ JP 2020-084919--

Signed and Sealed this
Thirtieth Day of May, 2023

Katherine Kelly Vidal
Director of the United States Patent and Trademark Office